United States Patent
Abdelghani et al.

(10) Patent No.: US 11,465,951 B2
(45) Date of Patent: Oct. 11, 2022

(54) DIMERIZATION OF CYCLOPENTADIENE USING SHELL AND TUBE HEAT EXCHANGER

(71) Applicant: SABIC GLOBAL TECHNOLOGIES B.V., Bergen op Zoom (NL)

(72) Inventors: Mohamed Sabri Abdelghani, Riyadh (SA); Ernesto Uehara, Riyadh (SA)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 17/311,865

(22) PCT Filed: Dec. 9, 2019

(86) PCT No.: PCT/IB2019/060578
§ 371 (c)(1),
(2) Date: Jun. 8, 2021

(87) PCT Pub. No.: WO2020/121171
PCT Pub. Date: Jun. 18, 2020

(65) Prior Publication Data
US 2022/0017435 A1  Jan. 20, 2022

Related U.S. Application Data (60) Provisional application No. 62/778,568, filed on Dec. 12, 2018.

(51) Int. Cl.
*C07C 2/50* (2006.01)
*F28D 7/10* (2006.01)
*C07C 13/61* (2006.01)

(52) U.S. Cl.
CPC ............. *C07C 2/50* (2013.01); *F28D 7/10* (2013.01); *C07C 2603/68* (2017.05)

(58) Field of Classification Search
CPC ....... C07C 2/50; C07C 2603/68; C07C 13/61; F28D 7/10
See application file for complete search history.

(56) References Cited

U.S. PATENT DOCUMENTS 2,813,135 A   11/1957   Johnson et al.
2,925,319 A   2/1960    Groll
(Continued)

FOREIGN PATENT DOCUMENTS

CN   200988827   12/2007
CN   101209948   7/2008
(Continued)

OTHER PUBLICATIONS

Hossain et al., "Thermal Characteristics of Heat Exchanger Type Chemical Reactors" *Journal of Chemical Engineering of Japan* 1985, 18(3), 193-199.

(Continued)

*Primary Examiner* — Philip Y Louie
*Assistant Examiner* — Jason Y Chong
(74) *Attorney, Agent, or Firm* — Norton Rose Fulbright US LLP (57) ABSTRACT

Systems and methods for producing dicyclopentadiene via thermal dimerization of cyclopentadiene. The feed stream comprising cyclopentadiene is flowed through four shell and tube heat exchangers in series. Each of the shell and tube heat exchangers comprise a shell and one or more tubes disposed in the shell. The feed stream is flowed in the tubes while the heat transfer medium is flowed in the shell to absorb the exothermic heat released by the dimerization of cyclopentadiene in the tubes. In this way, the temperature in the tubes is controlled at a level where the conversion rate of cyclopentadiene is above 99% and the occurrence of runaway reaction is substantially prevented.

20 Claims, 3 Drawing Sheets

(56) References Cited

U.S. PATENT DOCUMENTS

| | | |
|---|---|---|
| 3,196,188 A | 7/1965 | Parrish et al. |
| 3,700,741 A | 10/1972 | Aubrey et al. |
| 8,092,747 B2 | 1/2012 | Piccolo et al. |
| 9,522,374 B2 | 12/2016 | Olbert et al. |
| 2009/0010821 A1 | 1/2009 | Lehr |

FOREIGN PATENT DOCUMENTS

| | | |
|---|---|---|
| CN | 101450886 | 6/2009 |
| CN | 101928197 | 12/2010 |
| CN | 201720057 | 1/2011 |
| CN | 102276409 | 12/2011 |
| CN | 101671224 | 5/2013 |
| CN | 202953963 | 5/2013 |
| CN | 103664472 | 3/2014 |
| EP | 0509445 | 1/1996 |
| EP | 0734365 | 3/1999 |
| EP | 1358441 | 9/2007 |
| EP | 2178627 | 4/2010 |
| EP | 2231324 | 6/2016 |
| GB | 1375320 | 11/1974 |
| JP | H 05309258 | 11/1993 |
| RO | 63937 | 9/1978 |
| RU | 2538954 | 1/2015 |
| WO | WO 2010/144297 | 12/2010 |
| WO | WO 2016/064084 | 4/2016 |
| WO | WO 2016/140868 | 9/2016 |
| WO | WO 2017/174553 | 10/2017 |

OTHER PUBLICATIONS

International Search Report and Written Opinion issued in Corresponding PCT Application No. PCT/IB2019/060578, dated Mar. 23, 2020.

Jiaqi et al., "Formation of Dicyclopentadiene by Thermal Dimerization from C_5 Fractions" *Petrochemical Technology*, Apr. 1996, 1996. (Abstract only).

Song et al., "Design and optimization of dipolymer reactor in paralysis C_5" *Petrochemical Equipment Technology*, 34(4), 47-50, 2013.(Abstract only).

DIMERIZATION OF CYCLOPENTADIENE USING SHELL AND TUBE HEAT EXCHANGER

CROSS REFERENCE TO RELATED APPLICATIONS

This application is a national phase under 35 U.S.C. § 371 of International Application No. PCT/IB2019/060578, filed Dec. 9, 2019, which claims priority to and the benefit of U.S. Provisional Application No. 62/778,568, filed Dec. 12, 2018, the contents of each of which are incorporated into the present application in their entirety.

FIELD OF INVENTION

The present invention generally relates to systems and processes for producing dicyclopentadiene. More specifically, the present invention relates to systems and methods for producing dicyclopentadiene via thermal dimerization of cyclopentadiene in a reaction system comprising one or more shell and tube heat exchangers.

BACKGROUND OF THE INVENTION

Dicyclopentadiene is used as a highly reactive intermediate for producing resins such as unsaturated polyesters and aromatic hydrocarbons. Generally, dicyclopentadiene is formed by dimerization of cyclopentadiene, which is a component of pygas generated from steam cracking of naphtha. In a conventional process of cyclopentadiene dimerization, a tubular reactor is used to provide a relatively long residence time that is sufficient to achieve a high conversion rate. The tubular reactor is typically surrounded by a large heat sink medium because the cyclopentadiene dimerization is highly exothermic. Some systems include a large tank with one or more impellers to quickly mix the liquid and dissipate the heat generated during the dimerization reaction.

However, the economic feasibility of the conventional cyclopentadiene dimerization process is relatively limited. First of all, for the conventional method to achieve a cyclopentadiene conversion rate of above 50%, the energy demand is relatively high as the reactor has to be kept at an elevated reaction temperature for an extended period to achieve the required long residence time. Furthermore, the high reaction temperature can cause a substantial heat release from the highly exothermic dimerization reaction, resulting in runaway reaction in the reaction system. Thus, overall, the energy consumption of the conventional dimerization method is high. Meanwhile, for stirred-tank reactors with impellers, operating impellers demand a large amount of energy. Moreover, impellers cannot sufficiently mix the liquid in cyclopentadiene dimerization reactor, and such mixing forms hot spots in the liquid in the reactor. These hot spots not only limit the conversion rate of cyclopentadiene, but also induce side reactions for cyclopentadiene to form higher polymers other than dimers.

Overall, while systems and methods for producing dicyclopentadiene via dimerization reaction exist, the need for improvements in this field persists in light of at least aforementioned drawbacks for the conventional systems and methods.

BRIEF SUMMARY OF THE INVENTION

A solution to at least some of the above-mentioned problems associated with the production system and process for dicyclopentadiene via thermal dimerization has been discovered. The solution resides in a method of producing dicyclopentadiene in four serial shell and tube heat exchangers that provide large heat exchange area and a large volumetric ratio of heat exchange medium to reaction mixture in four reaction stages. Notably, the heat exchange medium can be controlled at a temperature that results in high conversion rate of cyclopentadiene. Further, the temperature control mechanism, and the configuration of the shell and tube heat exchangers are capable of effectively mitigating the temperature rises caused by large exothermic heat released by the dimerization reaction, thereby preventing the occurrence of runaway reaction in the reaction system. Therefore, the method of the present invention provides a technical solution to at least some of the problems associated with the currently available methods for producing dicyclopentadiene.

Embodiments of the invention include a method of producing dicyclopentadiene. The method comprises a first stage that comprises flowing a feed stream comprising cyclopentadiene monomer through first tubes of a first shell and tube heat exchanger. The temperature of the feed stream as it enters the first tubes is in a range of 40 to 60° C. The first tubes comprise fins. The first stage further comprises flowing a heat transfer medium through a first shell of the first shell and tube heat exchanger in the same direction as the flow of the feed stream. The temperature of the heat transfer medium as it enters the first shell is in a range of 65 to 80° C. The first stage further comprises subjecting the feed stream in the first tubes to reaction conditions sufficient to dimerize the cyclopentadiene monomer to form dicyclopentadiene. The temperature of a first stage effluent as it exits the first tubes is in a range of 80 to 90° C. The method further comprises a second stage that comprises cooling the first stage effluent to produce a second stage effluent at a temperature of 90 to 100° C. The method further comprises a third stage that comprises cooling the second stage effluent to produce a third stage effluent at a temperature of 110 to 120° C. The method further still comprise a fourth stage that comprises cooling the third stage effluent to produce a fourth stage effluent at a temperature of 120 to 130° C. Each of the first stage, the second stage, the third stage, and the fourth stage is carried out in a different shell and tube heat exchanger.

Embodiments of the invention include a method of producing dicyclopentadiene. The method comprises a first stage that comprises flowing a feed stream comprising cyclopentadiene monomer through first tubes of a first shell and tube heat exchanger. The temperature of the feed stream as it enters the first tubes is in a range of 40 to 60° C. The first tubes comprise fins. The first stage further comprises flowing a heat transfer medium through a first shell of the first shell and tube heat exchanger in the same direction as the flow of the feed stream. The temperature of the heat transfer medium as it enters the first shell is in a range of 65 to 80° C. The first stage further comprises subjecting the feed stream in the first tubes to reaction conditions sufficient to dimerize the cyclopentadiene monomer to form dicyclopentadiene, wherein temperature of a first stage effluent as it exits the first tubes is in a range of 80 to 90° C. A temperature of the heat transfer medium as it exists the first shell is in a range of 70 to 80° C. The method further comprises a second stage that comprises cooling the first stage effluent to produce a second stage effluent at a temperature of 90 to 100° C. The method further comprises a third stage that comprises cooling the second stage effluent to produce a third stage effluent at a temperature of 110 to 120° C. The method further still comprises a fourth stage that comprises cooling the third stage effluent to produce a fourth stage effluent at a temperature of 120 to 130° C. Each of the first stage, the second stage, the third stage, and the fourth stage is carried out in a different horizontal shell and tube heat exchanger.

The following includes definitions of various terms and phrases used throughout this specification.

The terms "about" or "approximately" are defined as being close to as understood by one of ordinary skill in the art. In one non-limiting embodiment the terms are defined to be within 10%, preferably, within 5%, more preferably, within 1%, and most preferably, within 0.5%.

The terms "wt. %", "vol. %" or "mol. %" refer to a weight, volume, or molar percentage of a component, respectively, based on the total weight, the total volume, or the total moles of material that includes the component. In a non-limiting example, 10 moles of component in 100 moles of the material is 10 mol. % of component.

The term "substantially" and its variations are defined to include ranges within 10%, within 5%, within 1%, or within 0.5%.

The terms "inhibiting" or "reducing" or "preventing" or "avoiding" or any variation of these terms, when used in the claims and/or the specification, includes any measurable decrease or complete inhibition to achieve a desired result.

The term "effective," as that term is used in the specification and/or claims, means adequate to accomplish a desired, expected, or intended result.

The term "runaway reaction(s)," as that term is used in the specification and/or claims, means a thermally unstable reaction system which exhibits an uncontrolled accelerating rate of reaction, which leads to rapid increases in temperature and/or pressure.

The use of the words "a" or "an" when used in conjunction with the term "comprising," "including," "containing," or "having" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The process of the present invention can "comprise," "consist essentially of," or "consist of" particular ingredients, components, compositions, etc., disclosed throughout the specification.

The term "primarily," as that term is used in the specification and/or claims, means greater than any of 50 wt. %, 50 mol. %, and 50 vol. %. For example, "primarily" may include 50.1 wt. % to 100 wt. % and all values and ranges there between, 50.1 mol. % to 100 mol. % and all values and ranges there between, or 50.1 vol. % to 100 vol. % and all values and ranges there between.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from one embodiment may be combined with features from any of the other embodiments. In further embodiments, additional features may be added to the specific embodiments described herein.

BRIEF DESCRIPTION OF THE DRAWINGS

For a more complete understanding, reference is now made to the following descriptions taken in conjunction with the accompanying drawings, in which:

FIG. 3A and FIG. 3B show simulation results of conversion rate of cyclopentadiene and temperature of reaction mixture against the length of the tubes in a shell and tube heat exchanger.

DETAILED DESCRIPTION OF THE INVENTION

Currently, the method of producing dicyclopentadiene via dimerization of cyclopentadiene suffers several problems including low conversion rate and runaway reactions in the production system. The low conversion rate of cyclopentadiene can significantly increase the production cost of dicyclopentadiene. The occurrence of runaway reactions can cause the total shut down of the production system. The present invention provides a solution to at least some of these problems. The solution is premised on a method of producing dicyclopentadiene that comprises four stages, each of which is carried out in a shell and tube heat exchanger comprising fins on the tubes. The method provides a large heat transfer surface area and a large volumetric ratio of heat transfer medium to reaction mixture to absorb the exothermic heat released from the dimerization of cyclopentadiene. Additionally, the temperature of the heat transfer medium is controlled at a higher temperature than it is in a conventional method to achieve a higher conversion rate and prevent the occurrence of runaway reaction in the production system. Therefore, the method of the present invention is capable of improving the production efficiency of dicyclopentadiene. These and other non-limiting aspects of the present invention are discussed in further detail in the following sections.

A. System for Producing Dicyclopentadiene

Figure 1:
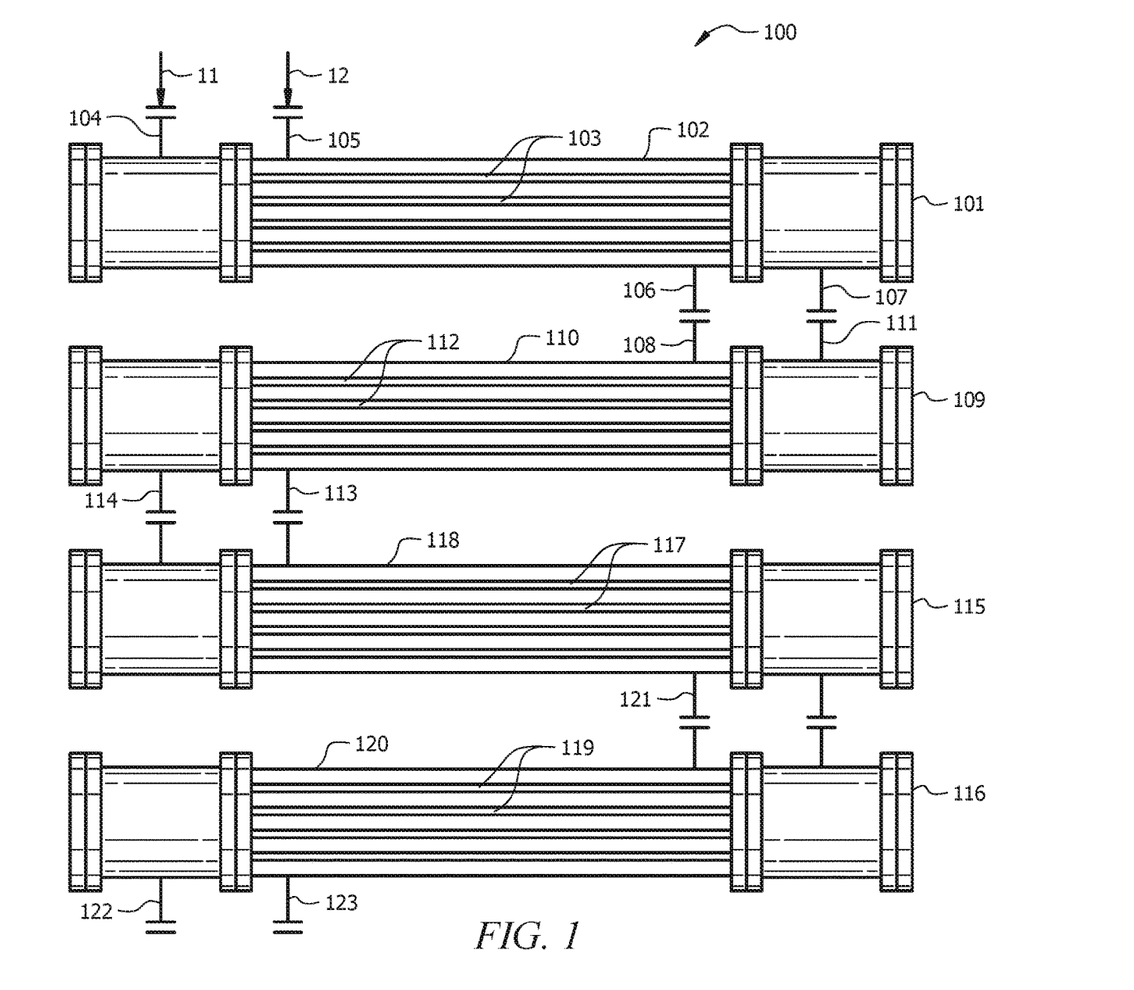
FIG. 1 shows a schematic diagram of a system for producing dicyclopentadiene, according to embodiments of the invention.

In embodiments of the invention, the system for producing dicyclopentadiene via dimerization of cyclopentadiene can include four shell and tube heat exchangers in series. With reference to FIG. 1, a schematic diagram is shown of system 100 that is capable of producing dicyclopentadiene with improved production efficiency and minimized occurrence of runaway reaction. According to embodiments of the invention, system 100 includes first shell and tube heat exchanger 101 adapted to receive feed stream 11 and heat transfer medium stream 12. In embodiments of the invention, feed stream 11 comprises cyclopentadiene. Heat transfer medium stream 12 may comprise water. According to embodiments of the invention, the water in heat transfer medium stream 12 may be chemically treated water or filtered water.

In embodiments of the invention, first shell and tube heat exchanger 101 includes shell 102 and one or more first tubes 103 disposed within first shell 102. According to embodiments of the invention, first shell and tube heat exchanger 101 further comprises first feed inlet 104 disposed on one end of shell and tube heat exchanger 101. First feed inlet 104 may be adapted to receive feed stream 11 into one or more first tubes 103. First shell and tube heat exchanger 101 may further comprise medium inlet 105 disposed on the same end of shell and tube heat exchanger 101. First medium outlet 105 may be adapted to receive heat transfer medium stream 12 into first shell 102.

In embodiments of the invention, each of one or more first tubes 103 includes fins for additional heat exchange surface area. Each of tubes 103 may comprise 6 to 10 fins and all ranges and values there between including 7, 8, and 9 fins. One or more first tubes 103 may have a surface to volume ratio of 50 to 150 $m^2/m^3$ and all ranges and values there between including 50 to 55 $m^2/m^3$, 55 to 60 $m^2/m^3$, 60 to 65 $m^2/m^3$, 65 to 70 $m^2/m^3$, 70 to 75 $m^2/m^3$, 75 to 80 $m^2/m^3$, 80 to 85 $m^2/m^3$, 85 to 90 $m^2/m^3$, 90 to 95 $m^2/m^3$, 95 to 100 $m^2/m^3$, 100 to 105 $m^2/m^3$, 105 to 110 $m^2/m^3$, 110 to 115 $m^2/m^3$, 115 to 120 $m^2/m^3$, 120 to 125 $m^2/m^3$, 125 to 130 $m^2/m^3$, 130 to 135 $m^2/m^3$, 135 to 140 $m^2/m^3$, 140 to 145 $m^2/m^3$, and 145 to 150 $m^2/m^3$. In embodiments of the invention, one or more first tubes 103 may have a substantially round sectional surface with a diameter to length ratio in a range of 0.0010 to 0.0020 and all ranges and values there between including 0.0011, 0.0012, 0.0013, 0.0014, 0.0015, 0.0016, 0.0017, 0.0018, and 0.0019. In embodiments of the invention, first tubes 103 may have a heat transfer coefficient in a range of 250 to 1000 $kJ\,m^{-2}\,hr^{-1}\,K^{-1}$ and all ranges and values there between including ranges of 250 to 300 $kJ\,m^{-2}\,hr^{-1}\,K^{-1}$, 300 to 350 $kJ\,m^{-2}\,hr^{-1}\,K^{-1}$, 350 to 400 $kJ\,m^{-2}\,hr^{-1}\,K^{-1}$, 400 to 450 $kJ\,m^{-2}\,hr^{-1}\,K^{-1}$, 450 to 500 $kJ\,m^{-2}\,hr^{-1}\,K^{-1}$, 500 to 550 $kJ\,m^{-2}\,hr^{-1}\,K^{-1}$, 550 to 600 $kJ\,m^{-2}\,hr^{-1}\,K^{-1}$, 600 to 650 $kJ\,m^{-2}\,hr^{-1}\,K^{-1}$, 650 to 700 $kJ\,m^{31\,2}\,hr^{-1}\,K^{-1}$, 700 to 750 $kJ\,m^{-2}\,hr^{-1}\,K^{-1}$, 750 to 800 $kJ\,m^{-2}\,hr^{-1}\,K^{-1}$, 800 to 850 $kJ\,m^{-2}\,hr^{-1}\,K^{-1}$, 850 to 900 $kJ\,m^{-2}\,hr^{-1}\,K^{-1}$, 900 to 950 $kJ\,m^{-2}\,hr^{-1}\,K^{-1}$, and 950 to 1000 $kJ\,m^{-2}\,hr^{-1}\,K^{-1}$. According to embodiments of the invention, one or more tubes 103 may comprise fins disposed on its outer circumference. One or more first tubes 103 may be made from materials comprising stainless steel, carbon steel, or combinations thereof. According to embodiments of the invention, a ratio of volume of first shell 102 to combined volumes of first tubes 103 may be in a range of 5 to 20 and all ranges and values there between including 5 to 6, 6 to 7, 7 to 8, 8 to 9, 9 to 10, 10 to 11, 11 to 12, 12 to 13, 13 to 14, 14 to 15, 15 to 16, 16 to 17, 17 to 18, 18 to 19, and 19 to 20. According to embodiments of the invention, first shell and tube heat exchanger 101 may comprise first medium outlet 106 disposed on the end of first shell and tube heat exchanger 101 that is distal from first medium outlet 106. First medium outlet 106 may be adapted to release heat transfer medium from shell 102. First shell and tube heat exchanger 101 may further comprise first reaction mixture outlet 107 disposed on the end of first shell and tube heat exchanger 101 that is distal from first feed inlet 104.

In embodiments of the invention, medium outlet 106 of first shell and tube heat exchanger 101 are in fluid communication with second medium inlet 108 of second shell and tube heat exchanger 109 such that heat transfer medium flows from first shell and tube heat exchanger 101 to second shell 110 of second shell and tube heat exchanger 109. Second shell and tube heat exchanger 109 may further comprise second reaction mixture inlet 111 adapted to receive reaction mixture from one or more tubes 103 of first shell and tube heat exchanger 101 to one or more second tubes 112 of second shell and tube heat exchanger 109. According to embodiments of the invention, second shell and tube heat exchanger 109 comprises second medium outlet 113 adapted to release heat transfer medium from shell 112. Second shell and tube heat exchanger 109 may comprise second reaction mixture outlet 114 adapted to release reaction medium from one or more tubes 112 of second shell and tube heat exchanger 109.

According to embodiments of the invention, one or more of second tubes 112 of second shell and tube heat exchanger 109 may have a surface to volume ratio of 50 to 150 $m^2/m^3$ and all ranges and values there between including 50 to 55 $m^2/m^3$, 55 to 60 $m^2/m^3$, 60 to 65 $m^2/m^3$, 65 to 70 $m^2/m^3$, 70 to 75 $m^2/m^3$, 75 to 80 $m^2/m^3$, 80 to 85 $m^2/m^3$, 85 to 90 $m^2/m^3$, 90 to 95 $m^2/m^3$, 95 to 100 $m^2/m^3$, 100 to 105 $m^2/m^3$, 105 to 110 $m^2/m^3$, 110 to 115 $m^2/m^3$, 115 to 120 $m^2/m^3$, 120 to 125 $m^2/m^3$, 125 to 130 $m^2/m^3$, 130 to 135 $m^2/m^3$, 135 to 140 $m^2/m^3$, 140 to 145 $m^2/m^3$, and 145 to 150 $m^2/m^3$. In embodiments of the invention, each of second tubes 112 of second shell and tube heat exchanger 109 may have a substantially round sectional surface with a diameter to length ratio in a range of 0.0010 to 0.0020 and all ranges and values there between including 0.0011, 0.0012, 0.0013, 0.0014, 0.0015, 0.0016, 0.0017, 0.0018, and 0.0019. In embodiments of the invention, one or more second tubes 112 of second shell and tube heat exchanger 109 may have a heat transfer coefficient in a range of 250 to 1000 $kJ\,m^{-2}\,hr^{-1}\,K^{-1}$ and all ranges and values there between including 250 to 300 $kJ\,m^{-2}\,hr^{-1}\,K^{-1}$, 300 to 350 $kJ\,m^{-2}\,hr^{-1}\,K^{-1}$, 350 to 400 $kJ\,m^{-2}\,hr^{-1}\,K^{-1}$, 400 to 450 $kJ\,m^{-2}\,hr^{-1}\,K^{-1}$, 450 to 500 $kJ\,m^{-2}\,hr^{-1}\,K^{-1}$, 500 to 550 $kJ\,m^{-2}\,hr^{-1}\,K^{-1}$, 550 to 600 $kJ\,m^{-2}\,hr^{-1}\,K^{-1}$, 600 to 650 $kJ\,m^{-2}\,hr^{-1}\,K^{-1}$, 650 to 700 $kJ\,m^{-2}\,hr^{-1}\,K^{-1}$, 700 to 750 $kJ\,m^{-2}\,hr^{-1}\,K^{-1}$, 750 to 800 $kJ\,m^{-2}\,hr^{-1}\,K^{-1}$, 800 to 850 $kJ\,m^{-2}\,hr^{-1}\,K^{-1}$, 850 to 900 $kJ\,m^{-2}\,hr^{-1}\,K^{-1}$, 900 to 950 $kJ\,m^{-2}\,hr^{-1}\,K^{-1}$, and 950 to 1000 $kJ\,m^{-2}\,hr^{-1}\,K^{-1}$. In embodiments of the invention, one or more second tubes 112 of second shell and tube heat exchanger 109 may comprise fins there around. One or more tubes 112 of second shell and tube heat exchanger 109 may be made of materials comprising stainless steel, carbon steel, or combinations thereof. According to embodiments of the invention, a ratio of volume of second shell 110 to combined volume of second tubes 112 of second shell and tube heat exchanger 109 may be in a range of 5 to 20 and all ranges and values there between 5 to 6, 6 to 7, 7 to 8, 8 to 9, 9 to 10, 10 to 11, 11 to 12, 12 to 13, 13 to 14, 14 to 15, 15 to 16, 16 to 17, 17 to 18, 18 to 19, and 19 to 20. In embodiments of the invention, second shell and tube heat exchanger 101 may be substantially the same as or different from first shell and tube heat exchanger 109.

In embodiments of the invention, system 100 may further include third shell and tube heat exchanger 115 and fourth shell and tube heat exchanger 116. According to embodiments of the invention, second shell and tube heat exchanger 109 may be in fluid communication with third shell and tube heat exchanger 115 such that reaction mixture from second tubes 112 of second shell and tube heat exchanger 109 flows to third tubes 117 of third shell and tube heat exchanger 115, and heat transfer medium flows from second shell 110 of second shell and tube heat exchanger 109 to third shell 118 of third shell and tube heat exchanger 115.

Similarly, third shell and tube heat exchanger 115 may be in fluid communication with fourth shell and tube heat exchanger 116 such that reaction mixture from third tubes 117 of third shell and tube heat exchanger 115 flows to fourth tubes 119 of fourth shell and tube heat exchanger 116, and heat transfer medium flows from third shell 118 of third shell and tube heat exchanger 115 to fourth shell 120 of third shell and tube heat exchanger 116. In embodiments of the invention, fourth shell and tube heat exchanger 116 may comprise product outlet 122 adapted to release reaction mixture (fourth stage effluent) from tubes 119 of fourth shell and tube heat exchanger 116. Fourth shell and tube heat exchanger 116 may further comprise fourth medium outlet 123 adapted to release heat transfer medium from shell 120 of fourth shell and tube heat exchanger 116.

According to embodiments of the invention, each of third shell and tube heat exchanger 115 and fourth shell and tube heat exchanger 116 may be substantially the same as or different from first shell and tube heat exchanger 101 and/or second shell and tube heat exchanger 109. In embodiments of the invention, each of third tubes 117 of third shell and tube heat exchanger 115 and fourth tubes 119 of fourth shell and tube heat exchanger 116 may have a surface to volume ratio of 50 to 150 $m^2/m^3$ and all ranges and values there between including ranges of 50 to 55 $m^2/m^3$, 55 to 60 $m^2/m^3$, 60 to 65 $m^2/m^3$, 65 to 70 $m^2/m^3$, 70 to 75 $m^2/m^3$, 75 to 80 $m^2/m^3$, 80 to 85 $m^2/m^3$, 85 to 90 $m^2/m^3$, 90 to 95 $m^2/m^3$, 95 to 100 $m^2/m^3$, 100 to 105 $m^2/m^3$, 105 to 110 $m^2/m^3$, 110 to 115 $m^2/m^3$, 115 to 120 $m^2/m^3$, 120 to 125 $m^2/m^3$, 125 to 130 $m^2/m^3$, 130 to 135 $m^2/m^3$, 135 to 140 $m^2/m^3$, 140 to 145 $m^2/m^3$, and 145 to 150 $m^2/m^3$. In embodiments of the invention, each of tubes 117 of third shell and tube heat exchanger 115 and tubes 119 of fourth shell and tube heat exchanger 116 may have a substantially round sectional surface with a diameter to length ratio in a range of 0.0010 to 0.0020 and all ranges and values there between including 0.0011, 0.0012, 0.0013, 0.0014, 0.0015, 0.0016, 0.0017, 0.0018, and 0.0019. Each of third tubes 117 of third shell and tube heat exchanger 115 and fourth tubes 119 of fourth shell and tube heat exchanger 116 may have a heat transfer coefficient in a range of 250 to 1000 $kJ\ m^{-2}\ hr^{-1}\ K^{-1}$ and all ranges and values there between including ranges of 250 to 300 $kJ\ m^{-2}\ hr^{-1}\ K^{-1}$, 300 to 350 $kJ\ m^{-2}\ hr^{-1}\ K^{-1}$, 350 to 400 $kJ\ m^{-2}\ hr^{-1}\ K^{-1}$, 400 to 450 $kJ\ m^{-2}\ hr^{-1}\ K^{-1}$, 450 to 500 $kJ\ m^{-2}\ hr^{-1}\ K^{-1}$, 500 to 550 $kJ\ m^{-2}\ hr^{-1}\ K^{-1}$, 550 to 600 $kJ\ m^{-2}\ hr^{-1}\ K^{-1}$, 600 to 650 $kJ\ m^{-2}\ hr^{-1}\ K^{-1}$, 650 to 700 $kJ\ m^{-2}\ hr^{-1}\ K^{-1}$, 700 to 750 $kJ\ m^{-2}\ hr^{-1}\ K^{-1}$, 750 to 800 $kJ\ m^{-2}\ hr^{-1}\ K^{-1}$, 800 to 850 $kJ\ m^{-2}\ hr^{-1}\ K^{-1}$, 850 to 900 $kJ\ m^{-2}\ hr^{-1}\ K^{-1}$, 900 to 950 $kJ\ m^{-2}\ hr^{-1}\ K^{-1}$, and 950 to 1000 $kJ\ m^{-2}\ hr^{-1}\ K^{-1}$. Each of third shell and tube heat exchanger 115 and fourth shell and tube heat exchanger 116 may have a shell to tube volumetric ratio of 5 to 20 and all ranges and values there between 5 to 6, 6 to 7, 7 to 8, 8 to 9, 9 to 10, 10 to 11, 11 to 12, 12 to 13, 13 to 14, 14 to 15, 15 to 16, 16 to 17, 17 to 18, 18 to 19, and 19 to 20. In embodiments of the invention, each of third tubes 117 of third shell and tube heat exchanger 115 and fourth tubes 119 of fourth shell and tube heat exchanger 116 may comprise stainless steel, carbon steel, or combinations thereof. In embodiments of the invention, first shell and tube heat exchanger 101, second shell and tube heat exchanger 109, third shell and tube heat exchanger 115, and fourth shell and tube heat exchanger 116 are horizontal heat exchangers. In each of the shell and tube heat exchanger, reaction mixture and heat transfer medium may be flowed in substantially the same direction.

According to embodiments of the invention, system 100 further includes a temperature control system adapted to maintain reaction temperature in first tubes 102, second tubes 112, third tubes 117, and fourth tubes 119 in a range of 40 to 130° C. and all ranges and values there between including ranges of 40 to 45° C., 45 to 50° C., 50 to 55° C., 55 to 60° C., 60 to 65° C., 65 to 70° C., 70 to 75° C., 75 to 80° C., 80 to 85° C., 85 to 90° C., 90 to 95° C., 95 to 100° C., 100 to 105° C., 105 to 110° C., 110 to 115° C., 115 to 120° C., 120 to 125° C., and 125 to 130° C. In embodiments of the invention, the temperature control system is adapted to adjust flow rate of heat transfer medium stream 12 and/or flow rate of feed stream 11 to control the reaction temperature in first tubes 103, second tubes 112, third tubes 117, and/or fourth tubes 119 to prevent occurrence of runaway reactions.

B. Method of Producing Dicyclopentadiene

Figure 2:
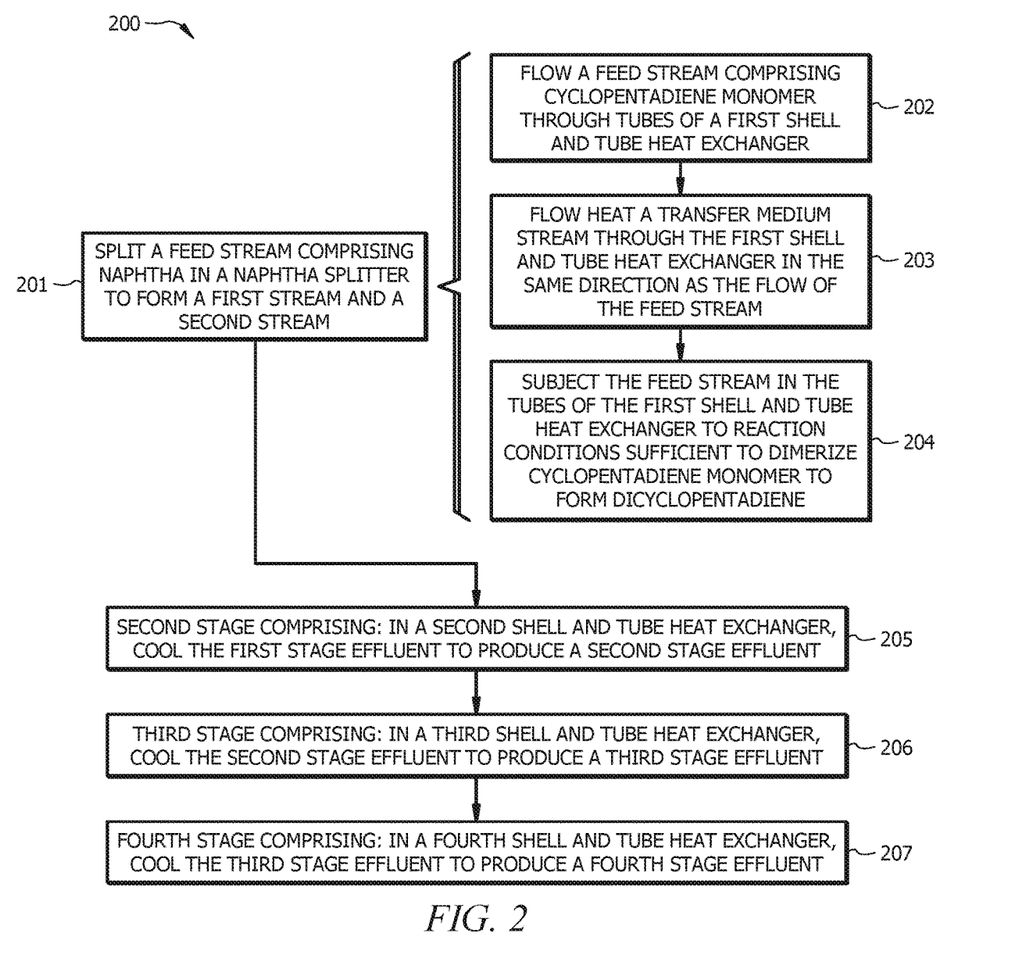
FIG. 2 shows a schematic flowchart of a method of producing dicyclopentadiene, according to embodiments of the invention.

Methods of producing dicyclopentadiene from cyclopentadiene have been discovered. The methods may be capable of improving the conversion rate of cyclopentadiene and substantially prevent occurrence of runaway reactions compared to conventional methods. As shown in FIG. 2, embodiments of the invention include method 200 for producing dicyclopentadiene via thermal dimerization. Method 200 may be implemented by system 100, as shown in FIG. 1. According to embodiments of the invention, method 200 may include a first stage (as shown in block 201), a second stage (as shown in block 205), a third stage (as shown in block 206), and a fourth stage (as shown in block 207). In embodiments of the invention, as shown in block 202, the first stage of method 200 includes flowing feed stream 11 comprising cyclopentadiene monomer through first tubes 103 of first shell and tube heat exchanger 101. In embodiments of the invention, temperature of feed stream 11 as it enters the first tubes is in a range of 40 to 60° C. and all ranges and values there between including ranges of 40 to 42° C., 42 to 44° C., 44 to 46° C., 46 to 48° C., 48 to 50° C., 50 to 52° C., 52 to 54° C., 54 to 56° C., 56 to 58° C., and 58 to 60° C. According to embodiments of the invention, each of first tubes 103 comprises 6 to 8 fins.

According to embodiments of the invention, as shown in block 203, the first stage of method 200 further includes flowing heat transfer medium stream 12 through first shell and tube heat exchanger 101 in the same direction as the flow of feed stream 11. The temperature of the heat transfer medium as it enters first shell 102 may be in a range of 65 to 80° C. and all ranges and values there between including the ranges of 65 to 68° C., 68 to 71° C., 71 to 74° C., 74 to 77° C., and 77 to 80° C. In embodiments of the invention, flow rate ratio of feed stream 11 to heat transfer medium is in a range of 0.01 to 0.05 and all ranges and values there between including 0.02, 0.03, and 0.04.

According to embodiments of the invention, as shown in block 204, first stage of method 200 further includes subjecting feed stream 11 in first tubes 103 to reaction conditions sufficient to dimerize cyclopentadiene monomer to form dicyclopentadiene. In embodiments of the invention, the reaction conditions include a reaction temperature in a range of 40 to 100° C. and all ranges and values there between including ranges of 40 to 45° C., 45 to 50° C., 50 to 55° C., 55 to 60° C., 60 to 65° C., 65 to 70° C., 70 to 75° C., 75 to 80° C., 80 to 85° C., 85 to 90° C., 90 to 95° C., and 95 to 100° C. Reaction conditions may further include a residence time of first shell and tubes heat exchanger 101 in a range of 0.3 to 0.6 minutes and all ranges and values there between including ranges of 0.3 to 0.35 minutes, 0.35 to 0.40 minutes, 0.40 to 0.45 minutes, 0.45 to 0.50 minutes, 0.50 to 0.55 minutes, and 0.55 to 0.60 minutes. In embodiments of the invention, first stage effluent exiting first reaction mixture outlet 107 comprises 55 to 65 wt. % dicyclopentadiene and all ranges and values there between 55 to 56 wt. %, 56 to 57 wt. %, 57 to 58 wt. %, 58 to 59 wt. %, 59 to 60 wt. %, 60 to 61 wt. %, 61 to 62 wt. %, 62 to 63 wt. %, 63 to 64 wt. %, and 64 to 65 wt. %.

In embodiments of the invention, as shown in block 205, method 200 includes a second stage that comprises, in second shell and tube heat exchanger 109, cooling the first stage effluent to produce a second stage effluent at a temperature of 90 to 110° C. and all ranges and values there between including the ranges of 90 to 92° C., 92 to 94° C., 94 to 96° C., 96 to 98° C., 98 to 100° C., 100 to 102° C., 102 to 104° C., 104 to 106° C., 106 to 108° C., and 108 to 110° C. In embodiments of the invention, the reaction mixture in second tubes 112 is kept at a temperature in a range of 80 to 125° C. and all ranges and values there between including ranges of 80 to 85° C., 85 to 90° C., 90 to 95° C., 95 to 100° C., 100 to 105° C., 105 to 110° C., 110 to 115° C., 115 to 120° C., and 120 to 125° C. The second stage effluent exiting second reaction mixture outlet 114 may comprise 80 to 90 wt. % dicyclopentadiene and all ranges and values there between including ranges of 80 to 81 wt. %, 81 to 82 wt. %, 82 to 83 wt. %, 83 to 84 wt. %, 84 to 85 wt. %, 85 to 86 wt. %, 86 to 87 wt. %, 87 to 88 wt. %, 88 to 89 wt. %, and 89 to 90 wt. %. Heat transfer medium in second shell 110 of second shell and tube heat exchanger 109 may be at a temperature of 90 to 100° C. and all ranges and values there between including ranges of 90 to 92° C., 92 to 94° C., 94 to 96° C., 96 to 98° C., and 98 to 100° C. According to embodiments of the invention, second shell and tube heat exchanger 109 is operated with a residence time in a range of 0.3 to 0.6 minutes and all ranges and values there between including ranges of 0.3 to 0.35 minutes, 0.35 to 0.40 minutes, 0.40 to 0.45 minutes, 0.45 to 0.50 minutes, 0.50 to 0.55 minutes, and 0.55 to 0.60 minutes.

In embodiments of the invention, as shown in block 206, method 200 includes a third stage that comprises cooling, in second shell and tube heat exchanger 109, the second stage effluent to produce a third stage effluent at a temperature of 115 to 125° C. and all ranges and values there between including 115 to 116° C., 116 to 117° C., 117 to 118° C., 118 to 119° C., 119 to 120° C., 120 to 121° C., 121 to 122° C., 122 to 123° C., 123 to 124° C., and 124 to 125° C. In embodiments of the invention, the reaction mixture in third tubes 117 may be kept at a temperature in a range of 100 to 125° C. and all ranges and values there between including ranges of 100 to 105° C., 105 to 110° C., 110 to 115° C., 115 to 120° C., and 120 to 125° C. The third stage effluent exiting third reaction mixture outlet 121 may comprise 90 to 96 wt. % dicyclopentadiene and all ranges and values there between including 91 wt. %, 92 wt. %, 93 wt. %, 94 wt. %, and 95 wt. %. Heat transfer medium in third shell 118 of third shell and tube heat exchanger 115 may be at a temperature of 110 to 120° C. and all ranges and values there between including ranges of 110 to 111° C., 111 to 112° C., 112 to 113° C., 113 to 114° C., 114 to 115° C., 115 to 116° C., 116 to 117° C., 117 to 118° C., 118 to 119° C., and 119 to 120° C. According to embodiments of the invention, third shell and tube heat exchanger 115 is operated with a residence time in a range of 0.3 to 0.6 minutes and all ranges and values there between including ranges of 0.3 to 0.35 minutes, 0.35 to 0.40 minutes, 0.40 to 0.45 minutes, 0.45 to 0.50 minutes, 0.50 to 0.55 minutes, and 0.55 to 0.60 minutes.

In embodiments of the invention, as shown in block 207, method 200 includes a fourth stage that comprises cooling, in fourth shell and tube heat exchanger 116, third stage effluent to produce a fourth stage effluent. In embodiments of the invention, the reaction mixture in fourth tubes 119 is kept at a temperature in a range of 125 to 140° C. and all ranges and values there between including ranges of 125 to 128° C., 128 to 131° C., 131 to 134° C., 134 to 137° C., 137 to 140° C. The fourth stage effluent (product stream) exiting fourth reaction mixture outlet 122 may comprise 96 to 99.8 wt. % dicyclopentadiene and all ranges and values there between including 96 to 96.4 wt. %, 96.4 to 96.8 wt. %, 96.8 to 97.2 wt. %, 97.2 to 97.6 wt. %, 97.6 to 98 wt. %, 98 to 98.4 wt. %, 98.4 to 98.8 wt. %, 98.8 to 99.2 wt. %, 99.2 to 99.6 wt. %, and 99.6 to 99.8 wt. %. Heat transfer medium in fourth shell 120 of fourth shell and tube heat exchanger 116 may be at a temperature of 120 to 140° C. and all ranges and values there between including ranges of 120 to 122° C., 122 to 124° C., 124 to 126° C., 126 to 128° C., 128 to 130° C., 130 to 132° C., 132 to 134° C., 134 to 136° C., 136 to 138° C., and 138 to 140° C. According to embodiments of the invention, fourth shell and tube heat exchanger 116 has a residence time in a range of 0.3 to 0.6 minutes and all ranges and values there between including ranges of 0.3 to 0.6 minutes and all ranges and values there between including ranges of 0.3 to 0.35 minutes, 0.35 to 0.40 minutes, 0.40 to 0.45 minutes, 0.45 to 0.50 minutes, 0.50 to 0.55 minutes, and 0.55 to 0.60 minutes.

According to embodiments of the invention, method 200 is capable of preventing occurrence of runaway reactions in system 100. In embodiments of the invention, dimerization reaction of cyclopentadiene occurs throughout all tubes of the fourth shell and tube heat exchangers. In method 200, cyclopentadiene may be converted at an overall conversion rate of 99.5 to 99.8% and all ranges and values there between including 99.6% and 99.7%.

Although embodiments of the present invention have been described with reference to blocks of FIG. 2, it should be appreciated that operation of the present invention is not limited to the particular blocks and/or the particular order of the blocks illustrated in FIG. 2. Accordingly, embodiments of the invention may provide functionality as described herein using various blocks in a sequence different than that of FIG. 2.

As part of the disclosure of the present invention, specific examples are included below. The examples are for illustrative purposes only and are not intended to limit the invention. Those of ordinary skill in the art will readily recognize parameters that can be changed or modified to yield essentially the same results.

EXAMPLE

Simulation on Temperatures in a Shell and Tube Heat Exchanger

Simulations on temperatures in tubes of a shell and tube heat exchanger were conducted. In the simulations, a cyclopentadiene feed stream was flowed through the tubes at an initial temperature of 50° C. with heat transfer medium flowed in the shell at an initial temperature of 80° C. The initial flow rate of the feed stream was 2.44 m$^3$/hr and the initial flow rate for the heat transfer medium was 68.33 m$^3$/hr. Each of the tube in the shell and tube heat exchangers included 8 fins, providing an additional 25% heat transfer area compared to non-fin tubes.

Figure 3A:
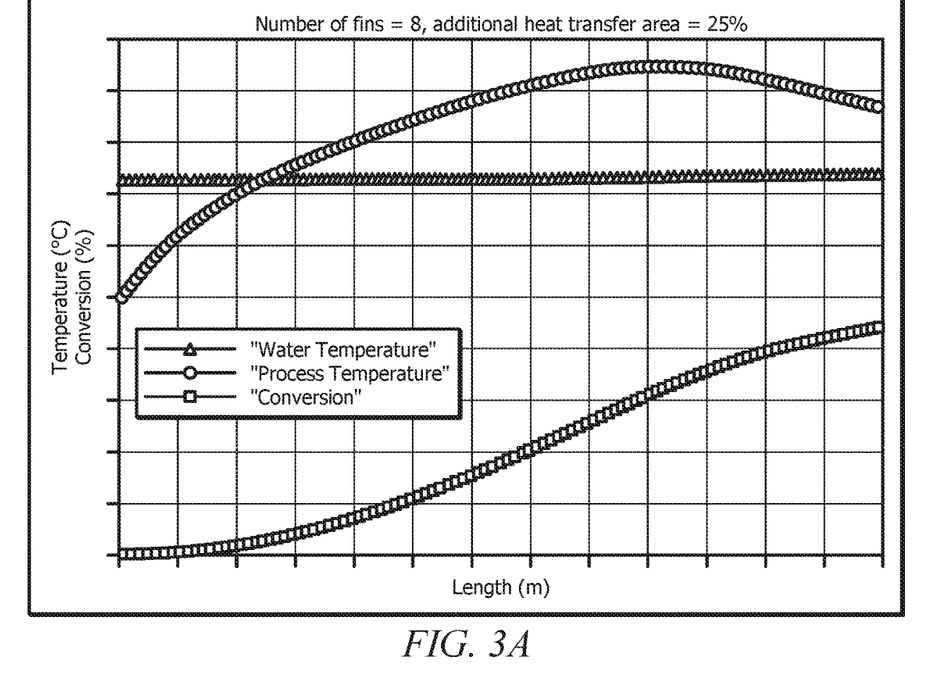
FIG. 3A shows the simulation results conducted for a shell and tube heat exchanger that comprises tubes with 8 fins.
Figure 3B:
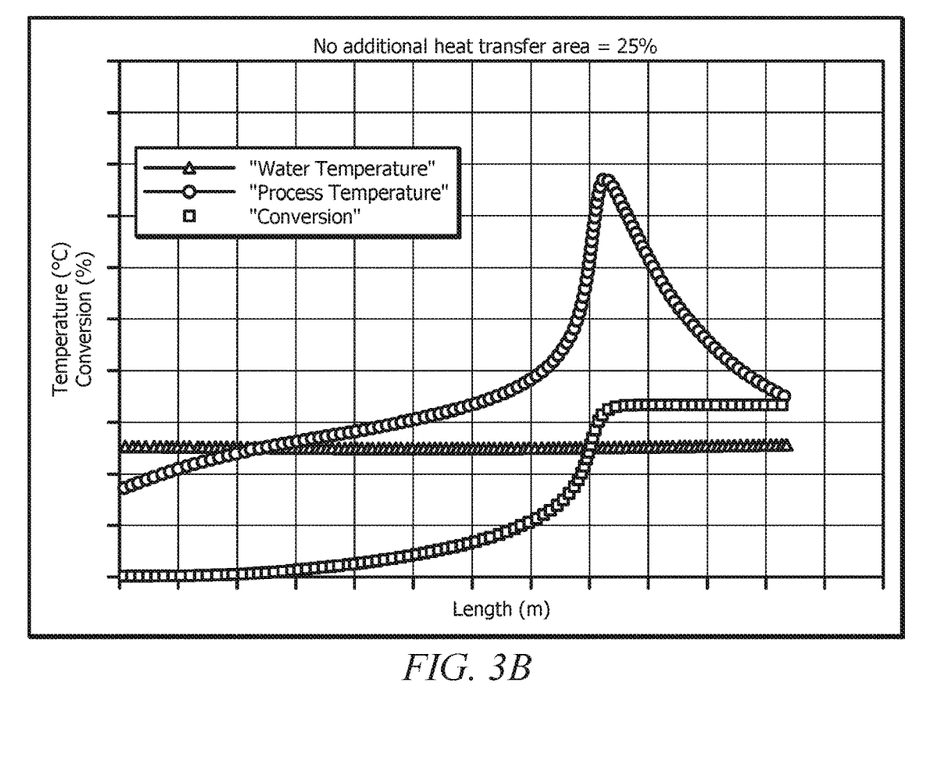
FIG. 3B shows the simulation results conducted for a shell and tube heat exchanger that comprises tube without fins.

The heat exchanger medium (water) temperature, the reaction mixture temperature in the tubes (process temperature), and the conversion rate of cyclopentadiene along the length of the tube were plotted for shell and tube heat exchangers comprising tubes with fins (FIG. 3A) and without fins (FIG. 3B). As shown in FIG. 3A, the temperature of the reaction mixture in the tubes plateaued and stayed relatively stable from about the middle point to the end of the shell and tube heat exchanger when the tubes included 8 fins. However, with the tubes that did not include fins, the temperature of reaction mixture in the tubes had a drastic spike and quick drop toward the end of the shell and tube heat exchanger, indicating possible occurrence of runaway reaction in the heat exchanger. Therefore, the shell and tube heat exchanger comprising 8-fin tubes showed superior temperature and conversion rate stability for carrying out thermal dimerization of cyclopentadiene.

In the context of the present invention, at least the following 15 embodiments are described. Embodiment 1 is a method of producing dicyclopentadiene. The method encompasses a first stage that includes flowing a feed stream containing cyclopentadiene monomer through first tubes of a first shell and tube heat exchanger, wherein temperature of the feed stream as it enters the first tubes is in a range of 40 to 60° C., wherein the first tubes comprise fins. The method also includes flowing a heat transfer medium through a first shell of the first shell and tube heat exchanger in the same direction as the flow of the feed stream, wherein temperature of the heat transfer medium as it enters the first shell is in a range of 65 to 80° C. The method additionally includes subjecting the feed stream in the first tubes to reaction conditions sufficient to dimerize the cyclopentadiene monomer to form dicyclopentadiene, wherein temperature of a first stage effluent as it exits the first tubes is in a range of 80 to 90° C. The method further includes a second stage that encompasses cooling the first stage effluent to produce a second stage effluent at a temperature of 90 to 110° C. In addition, the method includes a third stage that encompasses cooling the second stage effluent to produce a third stage effluent at a temperature of 110 to 120° C. The method further includes a fourth stage that encompasses cooling the third stage effluent to produce a fourth stage effluent at a temperature of 120 to 140° C., wherein the each of the first stage, the second stage, the third stage, and the fourth stage is carried out in a different shell and tube heat exchanger. Embodiment 2 is the method of embodiment 1, wherein a temperature of the heat transfer medium as it exists in the first shell is in a range of 65 to 80° C. Embodiment 3 is the method of either of embodiments 1 or 2, wherein each of the shell and tube heat exchanger corresponding to the first stage, the second stage, the third stage, and the fourth stage is a horizontal shell and tube heat exchanger. Embodiment 4 is the method of any of embodiments 1 to 3, wherein the fourth stage effluent contains more than 99.5 to 99.9 wt. % dicyclopentadiene. Embodiment 5 is the method of any of embodiments 1 to 4, wherein each of the shell and tube heat exchangers for the first stage, the second stage, the third stage, and the fourth stage is operated with a residence time of 0.3 to 0.6 minutes. Embodiment 6 is the method of any of embodiments 1 to 5, wherein the shell and tube heat exchangers for the first stage, the second stage, the third stage, and the fourth stage, are adapted to provide a heat exchange area in a range of 0.7 to 1.1 $m^2/m^3$. Embodiment 7 is the method of any of embodiments 1 to 6, wherein the heat exchange medium is selected from the group consisting of water, sea water, saline water, boiling water, or combinations thereof. Embodiment 8 is the method of embodiment 7, wherein the heat exchange medium comprising water is kept at a temperature lower than boiling point of water. Embodiment 9 is the method of either of embodiments 7 or 8, wherein the heat exchange medium comprising water is kept at a temperature of 65 to 130° C. Embodiment 10 is the method of any of embodiments 1 to 9, wherein the fluid in the tubes of the heat exchangers is flowed at a flowrate of 2 to 3 $m^3$/hr. Embodiment 11 is the method of any of embodiments 1 to 10, wherein the heat exchange medium in the shells of the heat exchangers is flowed at a flowrate of 3 to 75 $m^3$/hr. Embodiment 12 is the method of any of embodiments 1 to 11, wherein, in each heat exchanger, the fluid in the tubes and the heat exchange medium in the shells have a volumetric ratio of 0.03 to 1.0. Embodiment 13 is the method of any of embodiments 1 to 12, wherein the method is capable of substantially preventing occurrence of runaway reaction in the heat exchangers. Embodiment 14 is the method of any of embodiments 1 to 13, wherein the temperature change of the fluid in the tubes of the heat exchanger is in a range of 20 to 50° C. Embodiment 15 is the method of any of embodiments 1 to 14, wherein each of the first stage, the second stage, the third stage, and the fourth stage are configured to have a residence time and/or total heat exchanger tube length that allow the reaction to proceed under control to achieve maximum conversion.

Although embodiments of the present application and their advantages have been described in detail, it should be understood that various changes, substitutions and alterations can be made herein without departing from the spirit and scope of the embodiments as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the above disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A method of producing dicyclopentadiene, the method comprising:
   a first stage that comprises:
      flowing a feed stream comprising cyclopentadiene monomer through first tubes of a first shell and tube heat exchanger, wherein temperature of the feed stream as it enters the first tubes is in a range of 40 to 60° C., wherein the first tubes comprise fins;
      flowing a heat transfer medium through a first shell of the first shell and tube heat exchanger in the same direction as the flow of the feed stream, wherein a temperature of the heat transfer medium as it enters the first shell is in a range of 65 to 80° C.; and
      subjecting the feed stream in the first tubes to reaction conditions sufficient to dimerize the cyclopentadiene monomer to form dicyclopentadiene, wherein a temperature of a first stage effluent as it exits the first tubes is in a range of 80 to 90° C.;
   a second stage that comprises:
      flowing the first stage effluent through second tubes of a second shell and tube heat exchanger, wherein the second tubes comprise fins;

flowing the heat transfer medium, released from the first shell, through a second shell of the second shell and tube heat exchanger; and cooling the first stage effluent to produce a second stage effluent at a temperature of 90 to 110° C.; and a third stage that comprises:

flowing the second stage effluent through third tubes of a third shell and tube heat exchanger, wherein the third tubes comprises fins;

flowing the heat transfer medium, released from the second shell, through a third shell of the second shell and tube heat exchanger; and cooling the second stage effluent to produce a third stage effluent at a temperature of 110 to 120° C.; and a fourth stage that comprises:

flowing the third stage effluent through fourth tubes of a fourth shell and tube heat exchanger, wherein the fourth tubes comprise fins;

flowing the heat transfer medium, released from the third shell, through a fourth shell of the second shell and tube heat exchanger; and cooling the third stage effluent to produce a fourth stage effluent at a temperature of 120 to 140° C.

2. The method of claim 1, wherein a temperature of the heat transfer medium as it exists in the first shell is in a range of 65 to 80° C.

3. The method of claim 1, wherein each of the shell and tube heat exchanger corresponding to the first stage, the second stage, the third stage, and the fourth stage is a horizontal shell and tube heat exchanger.

4. The method of claim 3, wherein each of the first stage, the second stage, the third stage, and the fourth stage are configured to have a residence time and/or total heat exchanger tube length that allow the reaction to proceed under control to achieve maximum conversion.

5. The method of claim 1, wherein the fourth stage effluent comprises more than 99.5 to 99.9 wt. % dicyclopentadiene.

6. The method of claim 5, wherein each of the first stage, the second stage, the third stage, and the fourth stage are configured to have a residence time and/or total heat exchanger tube length that allow the reaction to proceed under control to achieve maximum conversion.

7. The method of claim 1, wherein each of the shell and tube heat exchangers for the first stage, the second stage, the third stage, and the fourth stage is operated with a residence time of 0.3 to 0.6 minutes.

8. The method of claim 7, wherein each of the first stage, the second stage, the third stage, and the fourth stage are configured to have a residence time and/or total heat exchanger tube length that allow the reaction to proceed under control to achieve maximum conversion.

9. The method of claim 1, wherein the shell and tube heat exchangers for the first stage, the second stage, the third stage, and the fourth stage, are adapted to provide a heat exchange area in a range of 0.7 to 1.1 $m^2/m^3$.

10. The method of claim 1, wherein the heat exchange medium is selected from the group consisting of water, sea water, saline water, boiling water, or combinations thereof.

11. The method of claim 10, wherein the heat exchange medium comprising water is kept at a temperature lower than boiling point of water.

12. The method of claim 10, wherein the heat exchange medium comprising water is kept at a temperature of 65 to 130° C.

13. The method of claim 1, wherein the feed stream in the tubes of the heat exchangers is flowed at a flowrate of 2 to 3 $m^3$/hr.

14. The method of claim 1, wherein the heat exchange medium in the shells of the heat exchangers is flowed at a flowrate of 3 to 75 $m^3$/hr.

15. The method of claim 1, wherein, in each heat exchanger, the feed stream in the tubes and the heat exchange medium in the shells have a volumetric ratio of 0.03 to 1.0.

16. The method of claim 1, wherein the method is capable of substantially preventing occurrence of runaway reaction in the heat exchangers.

17. The method of claim 1, wherein the temperature change of the feed stream in the tubes of the heat exchanger is in a range of 20 to 50° C.

18. The method of claim 1, wherein each of the first stage, the second stage, the third stage, and the fourth stage are configured to have a residence time and/or total heat exchanger tube length that allow the reaction to proceed under control to achieve maximum conversion.

19. The method of claim 1, wherein each of the first stage, the second stage, the third stage, and the fourth stage are configured to have a residence time that allows the reaction to proceed under control to achieve maximum conversion.

20. The method of claim 1, wherein each of the first stage, the second stage, the third stage, and the fourth stage are configured to have a total heat exchanger tube length that allow the reaction to proceed under control to achieve maximum conversion.

* * * * *